United States Patent [19]
Sommer et al.

[11] Patent Number: 5,999,858
[45] Date of Patent: Dec. 7, 1999

[54] MEDICAL ELECTRICAL LEAD

[75] Inventors: John L. Sommer, Coon Rapids; Rick D. McVenes, Isanti; Douglas Hine, White Bear Lake, all of Minn.

[73] Assignee: Medtronic, Inc., Minneapolis, Minn.

[21] Appl. No.: 09/196,860

[22] Filed: Nov. 20, 1998

Related U.S. Application Data

[62] Division of application No. 08/895,977, Jul. 17, 1997.

[51] Int. Cl.$^6$ ........................................................ A61N 1/05
[52] U.S. Cl. ............................................................ 607/122
[58] Field of Search ..................................... 607/116, 119, 607/122, 123, 125, 126, 128; 600/373, 374, 377, 381

[56] References Cited

U.S. PATENT DOCUMENTS

| | | | |
|---|---|---|---|
| 3,729,008 | 4/1973 | Berkovits | 607/125 |
| 4,033,357 | 7/1977 | Helland et al. . | |
| 4,154,247 | 5/1979 | O'Neill | 607/123 |
| 4,269,198 | 5/1981 | Stokes . | |
| 4,394,866 | 7/1983 | Hughes . | |
| 4,402,328 | 9/1983 | Doring . | |
| 4,402,330 | 9/1983 | Lindemans . | |
| 4,454,888 | 6/1984 | Gold . | |
| 4,506,680 | 3/1985 | Stokes . | |
| 4,627,439 | 12/1986 | Harris . | |
| 5,016,646 | 5/1991 | Gotthardt et al. . | |
| 5,074,313 | 12/1991 | Dahl et al. . | |
| 5,387,233 | 2/1995 | Alferness et al. . | |
| 5,408,744 | 4/1995 | Gates . | |
| 5,683,445 | 11/1997 | Swoyer . | |

*Primary Examiner*—William E. Kamm
*Assistant Examiner*—George R. Evanisko
*Attorney, Agent, or Firm*—Reed A. Duthler; Harold R. Patton

[57] ABSTRACT

A cardiac pacing lead for use in the coronary sinus and coronary veins. The lead is provided with a lead body configured to exhibit a curved configuration along a distal portion thereof, induced to maintain a portion of the curved configuration solely by a portion of a polyurethane lead body formed to display the curved configuration and wherein the lead conductor is freely mounted within the segment The curved configuration includes first and second arcuate segments together providing a single-plane curvature of approximately 180 degrees, separated by a generally straight segment, the first segment having a greater length and greater arc of curvature than the second segment. The lead body encloses a first conductive coil coupled to an electrode mounted to the distal end of the lead body and a second elongated conductive coil is also located within the lead body and extends to a transition point proximal to the distal end of the first coil conductor, the second coil terminating within the lead body and insulated from the exterior of the lead body. The first conductive coil has a generally straight configuration and the distal portion of the second coil is formed to define a curve.

9 Claims, 3 Drawing Sheets

MEDICAL ELECTRICAL LEAD

This application is a division of application Ser. No. 08/895,977, filed Jul. 17, 1997.

BACKGROUND OF THE INVENTION

The present invention relates to electrical medical leads generally and more particularly to implantable cardiac pacing and defibrillation leads.

Over the years, numerous leads have been designed for the purpose of pacing the atria. One basic approach has been to provide the lead with a pre-formed "J"-shape, adapted to result in the electrode at the tip of the lead being reliably located in the right atrial appendage. Various approaches to providing a J-shaped lead have included the provision of molded, curved polyurethane lead bodies or sheaths as in U.S. Pat. No. 4,394,866 issued to Hughes and U.S. Pat. No. 4,626,439 issued to Harris, curved silicone rubber sheaths as in U.S. Pat. No. 4,402,328 issued to Doring, curved coils as in U.S. Pat. No. 4,402,330 issued to Lindemans, and curved reinforcing wires as in U.S. Pat. No. 4,454,888 issued to Gold. Such curve providing structures are incorporated in the distal portion of the lead so that it maintains a J-shaped configuration after implant, allowing the electrode to continue to resiliently engage the right atrial appendage until such time as it is anchored in place by means of fibrotic tissue growth.

Pacing the atria has also been accomplished by means of electrode leads located in the coronary sinus. One of the earlier coronary sinus leads is the Medtronic, Inc. Model 6992 Coronary Sinus Lead which has a generally straight lead body, carrying two ring electrodes. More recently, leads having pre-formed curved configurations have been employed for pacing and/or mapping the electrical activity of the atria, including U.S. Pat. No. 5,423,772 issued to Lurie, U.S. Pat. No. 5,387,233 issued to Alferness et al., and commonly assigned application Ser. No. 08/638,458 filed Apr. 29, 1996 by Swoyer for a "Medical Electrical Lead" now U.S. Pat. No. 5,683,445.

SUMMARY OF THE INVENTION

The present invention is directed toward providing an optimized pacing lead for location in the coronary sinus/coronary veins of the human heart. The lead is provided with a J-shaped curve at its distal end, adapted to assist insertion of the lead into the coronary sinus and to maintain the lead in the coronary sinus after implant. The J-shaped configuration of the lead defines a curve extending generally in a single plane over an arc of about 180°. The arc is divided into major and minor segments, the major segment extending from the distal tip of the lead, over a curvature of about 135°, plus or minus 10° the minor segment extending over an arc of about 45°, plus or minus 10°. Separating the major and minor segments is a short, relatively straight transition zone.

The J-shaped curve is provided by means of a curved tubular polyurethane sheath in which the conductor coil is freely mounted, conjunction with a curved coil, which ends at the transition zone. Unlike previous J-shaped leads employing curved polyurethane sheaths, the distal portion of the lead defining the major segment of the curve is neither molded to the conductor coil as in the above cited Harris and Hughes patents nor provided with additional curve inducing or curve retaining mechanisms as in the above cited Doring and Lindemans patents. As such, after implant, the polyurethane sheath extending along the major segment readily takes a set corresponding to the internal configuration of the coronary sinus/coronary vein into which it has been inserted, which is believed to be beneficial in providing long term stability of the lead and in minimizing negative interactions between the lead and the heart tissue.

The lead is provided with an elongated straight conductor coil extending from an electrode mounted at the distal end of the lead to an electrical connector assembly located on the proximal end of the lead, and is provided with a second coil, coaxially mounted around and spaced from the conductor coil, extending from the electrical connector on the proximal end of the lead to the transition zone, where it terminates within the outer sheath of the lead. The second, outer coil is provided to enhance handling characteristics and the distal portion of the coil is curved to assist in defining the curvature of the minor segment of the J-shaped curve. There is no electrode associated with the termination of the second, outer coil. The distal end of the second coil is thus insulated from the exterior of the sheath.

DETAILED DESCRIPTION OF THE PREFERRED EMBODIMENT

Figure 1:
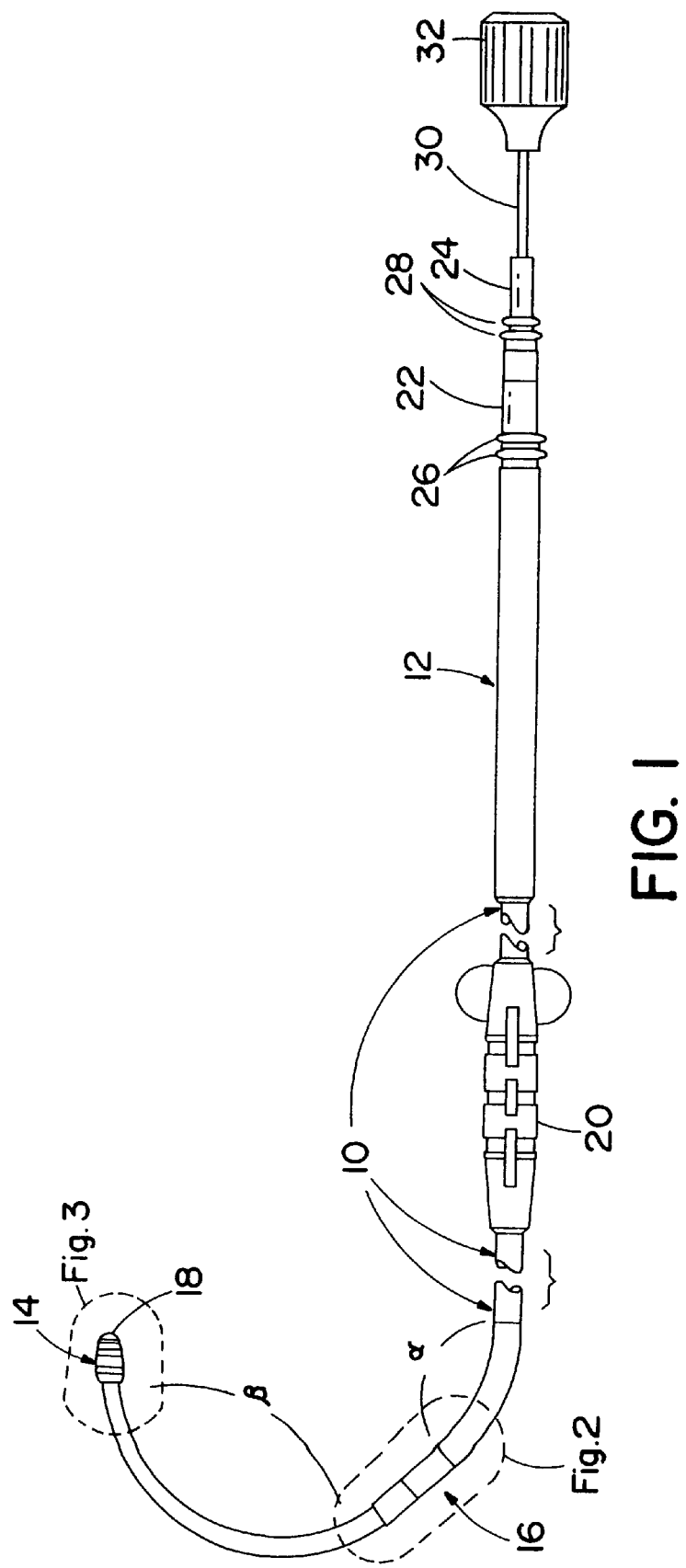
FIG. 1 is a plan view of a pacing lead according to the present invention.

FIG. 1 shows a plan view of a lead according to the present invention. The lead is provided with an elongated lead body 10 which carries a connector assembly 12 at its proximal end and a tip electrode 18 at its distal end 14. Tip electrode 18 is coupled to connector pin 24 by means of an elongated, coiled conductor. The coil in its relaxed condition should have a generally straight, non-curve configuration.

As illustrated, the lead of FIG. 1 is provided with a J-shaped bend over its distal section, including a first, minor arcuate segment α and a second, major arcuate segment β separated by a short generally straight transition zone 16. Overall, the arc of curvature provided by the major and minor segments should total approximately 180°. Preferably the minor segment α extends over approximately 45° with the major segment β extending over approximately 135°. The radius of curvature of the major segment β is preferably approximately 0.4 to 0.6 inches, with the radius of curvature of the minor segment α being somewhat greater, for example, about 0.6 to 0.8 inches. The generally straight transition zone 16 may have a length of approximately 0.2 inches.

Also mounted to the connector assembly 12 are a connector ring 22 and two sets of sealing rings 26 and 28. Connector ring 22 is connected to a second coiled conductor mounted coaxially around the conductor coupling pin 24 to electrode 14, but insulated therefrom. A stylet 30 with knob 32 is shown inserted into the lead. The stylet 30 is employed to straighten the lead body during insertion. An anchoring sleeve 20 is illustrated mounted around the lead body 10.

Figure 2:
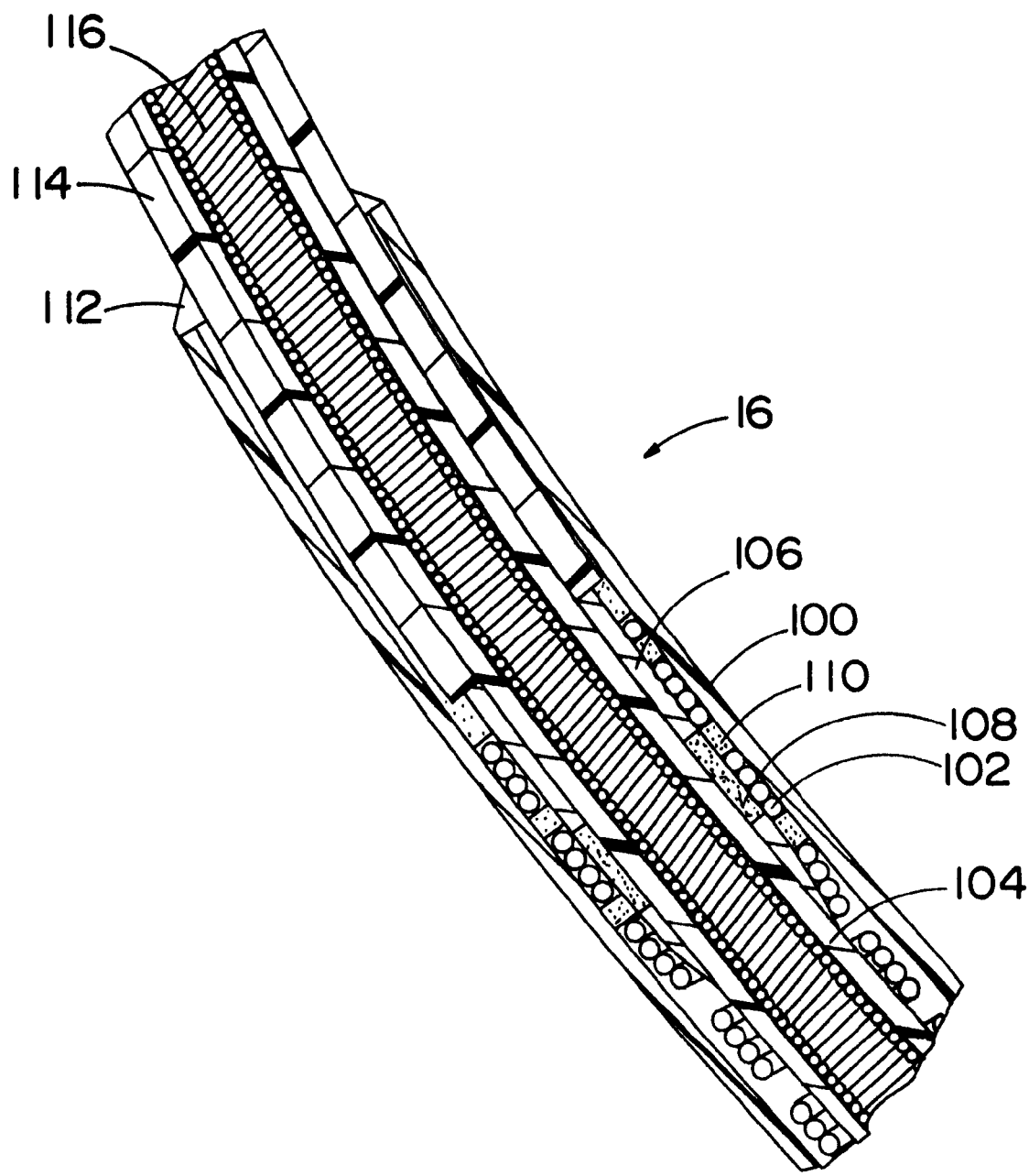
FIG. 2 is a sectional view through the transition zone of the lead illustrated in FIG. 1.

FIG. 2 is a sectional view through the transition section 16 of the lead illustrated in FIG. 1. In this view it can be seen that the lead body is provided with a proximal outer polyurethane insulative sheath 100 which extends back to the connector assembly 12 (FIG. 1) and terminates in the transition region 16. Proximal outer polyurethane sheath 100 surrounds the outer coil 102 which in a relaxed state assumes an approximately 45° bend along its axis as illustrated at its distal end and extends proximally therefrom in a generally straight configuration along its axis, to the connector ring 22 on the connector assembly 12 (FIG. 1), to which it is coupled. Outer coil 102 may take the form of a four filar coil of MP35 alloy, as presently employed in cardiac pacing leads. Coil 102 terminates at and is welded to a welding sleeve 106, which in turn is mounted around an inner insulative sheath 104, which extends distally to the tip electrode 18 (FIG. 1) and extends proximally to the connector assembly 12 (FIG. 1). Located within inner sheath 104 is coiled conductor 116 which may be a five filar coil of MP35N alloy, as presently employed in cardiac pacing leads and which extends distally to the electrode 18 and proximally to connector pin 24 (FIG. 1). Coiled conductor 116 is freely mounted within a tubular inner sheath 104 having smooth internal wall surfaces such that the conductor and inner wall of the sheath may move longitudinally relative to one another, for example as the lead is flexed or bent. The outer diameter of the inner coil is thus preferably no greater than the inner diameter of the sheath 104 and more preferably somewhat less than the inner diameter of the inner sheath 104. The outer distal outer polyurethane sheath 114 extends from the transition zone distally to electrode 18 (FIG. 1). The distal end of proximal outer sheath 100 is adhesively mounted to the proximal portion of distal outer sheath 114 by means of adhesive 112. A mechanical interlock of the components of the lead in the transition zone 16 is provided by means of an adhesive backfill 110, which fills the spaces between outer sheath 100 and welding sleeve 106 and outer coil 102 as well as filling apertures 108 provided in welding sleeve 106 and coupling to inner sheath 104.

Inner sheath 104, proximal outer sheath 100 and distal outer sheath 114 are heat set to assume the above described major and minor arcuate segments α and β illustrated in FIG. 1. Heat setting of the polyurethane sheaths provides the only mechanism for providing the J-shaped curvature illustrated in FIG. 1 for the major segment β at the distal end of the lead. As a result, after implantation of the lead for a period of time, the sheaths along the major segment β will take a set corresponding to the internal configuration of the coronary sinus and great vein in which they are inserted. This feature is believed to assist in retaining the lead in its desired location long term and in minimizing negative interactions between the lead and heart tissues.

Figure 3:
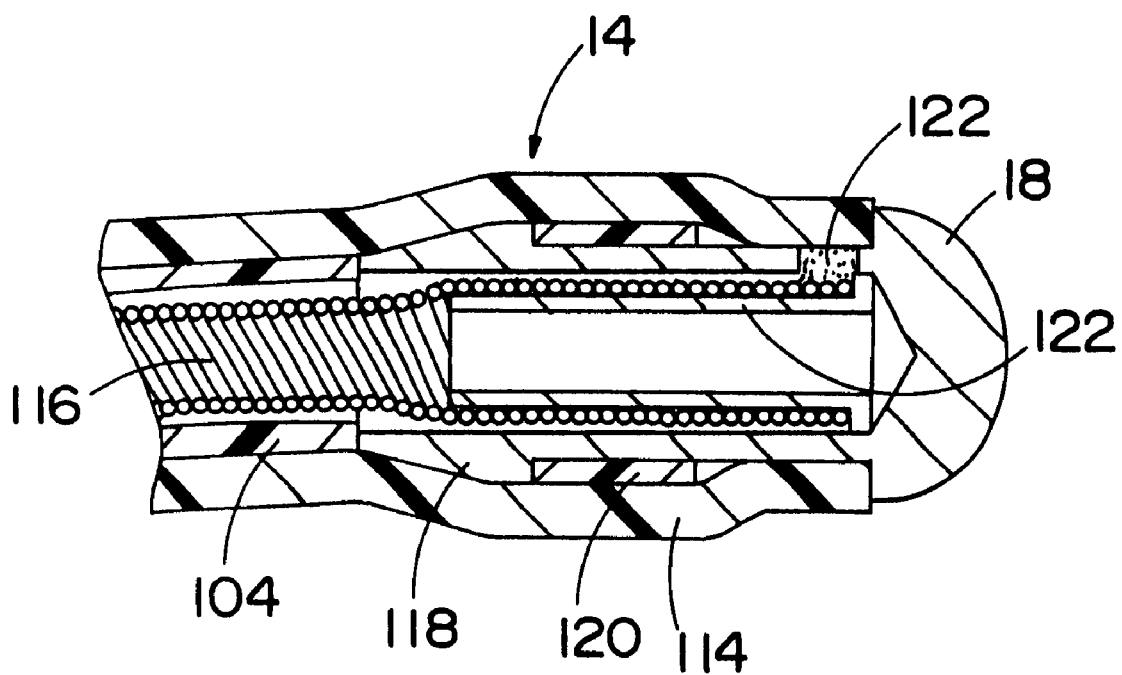
FIG. 3 is a sectional view through the lead of FIG. 1 in the vicinity of the tip electrode.

FIG. 3 is a sectional view the distal tip 14 of the lead illustrated in FIG. 1. In this view it can be seen that conductor 116 is coupled to electrode 18 by means of a crimping core 122. Electrode 18 may take the form of a hemispherical electrode formed of platinum provided with a coating of platinum black or may take the form of any of a numerous known types of cardiac pacing electrodes, including those disclosed in U.S. Pat. No. 5,408,744 issued to Gates, U.S. Pat. No. 5,074,313 issued to Dahl, U.S. Pat. No. 4,506,680 issued to Stokes, U.S. Pat. No. 4,269,198 issued to Stokes or U.S. Pat. No. 4,033,357 issued to Helland et al., all incorporated in by reference in their entireties.

The inner insulative sheath 104 terminates at the distal end of electrode shank 118, with distal outer sheath 114 extending over the shank 118. A polyurethane band 120 is heat shrunk around the shank 118, and adhesively bonded to the band 120. Adhesive 122 is backfilled through a bore in the shank 118 of electrode 18.

In conjunction with the above disclosure, we claim:

1. A cardiac pacing lead, comprising:
   an elongated conductor having proximal and distal ends;
   an electrical connector coupled to the proximal end of said conductor;
   an electrode coupled to the distal end of said conductor;
   an insulative lead body enclosing said conductor; and
   wherein said lead is formed to exhibit a curved configuration along a portion thereof; and
   wherein said curved configuration comprises first and second arcuate segments together providing a single-plane curvature of approximately 180 degrees, said first and second arcuate segments separated by a generally straight segment, said first segment having a greater length and greater arc of curvature than said second segment.

2. The lead according to claim 1 wherein said first segment is distal to said second segment.

3. The lead according to claim 2 wherein said lead body comprises a segment of said lead body extending along said first segment of the lead, formed to display said curved configuration.

4. The lead according to claim 3 wherein said lead body comprises a tubular polymer sheath enclosing said conductor, formed to display said curved configuration.

5. The lead according to claim 4 wherein said conductor is a coiled conductor which when relaxed extends along a generally straight axis.

6. The lead according to claim 1 or claim 2 or claim 3 or claim 4 or claim 5 wherein said lead body comprises a segment of said lead body extending along said second arcuate segment of the lead, formed to display said the arcuate curvature of the second arcuate segment and said lead further comprises an additional means for inducing said lead to exhibit the arcuate curvature of the second arcuate segment.

7. The lead according to claim 6 wherein said additional means comprises a metal member formed to display the arcuate curvature of the second arcuate segment.

8. The lead according to claim 7 wherein said metal member is a metal coil mounted within said lead body and having a distal termination located proximal to said first segment of the lead body.

9. The lead according to claim 8 wherein said metal coil extends proximally to a location adjacent to said electrical connector.

* * * * *